United States Patent
Byrum

(10) Patent No.: US 7,311,716 B2
(45) Date of Patent: Dec. 25, 2007

(54) SURGICALLY IMPLANTABLE ADJUSTABLE BAND HAVING A FLAT PROFILE WHEN IMPLANTED

(75) Inventor: Randal T. Byrum, Kings Mills, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 352 days.

(21) Appl. No.: 10/784,416

(22) Filed: Feb. 20, 2004

(65) Prior Publication Data
US 2005/0187566 A1 Aug. 25, 2005

(51) Int. Cl.
*A61B 17/08* (2006.01)
(52) U.S. Cl. ...................................... 606/151
(58) Field of Classification Search ............... 606/151, 606/153, 154, 156, 157; 600/37; 623/23.67
See application file for complete search history.

(56) References Cited

U.S. PATENT DOCUMENTS

| | | | |
|---|---|---|---|
| 4,592,339 A | 6/1986 | Kuzmak et al. | |
| 5,226,429 A | 7/1993 | Kuzmak | |
| 5,601,604 A | 2/1997 | Vincent | |
| RE36,176 E | 3/1999 | Kuzmak | |
| 6,102,922 A | 8/2000 | Jakobsson et al. | |
| 6,453,907 B1 | 9/2002 | Forsell | |
| 6,461,292 B1 | 10/2002 | Forsell | |
| 6,470,892 B1 | 10/2002 | Forsell | |
| 2003/0105385 A1 | 6/2003 | Forsell | |
| 2003/0114729 A1 | 6/2003 | Forsell | |

FOREIGN PATENT DOCUMENTS

| | | |
|---|---|---|
| EP | 1 036 545 A | 9/2000 |
| WO | WO 86/04498 A | 8/1986 |

OTHER PUBLICATIONS

EP Search Report dated Jun. 2, 2005 for EP Application No. 05250951.0.

*Primary Examiner*—Eduardo C. Robert
*Assistant Examiner*—Annette Reimers

(57) ABSTRACT

An implantable surgical device having a deployed shape and an undeployed shape. The device includes an elongated flexible inflatable balloon portion and an elongated flexible and substantially inextensible band portion. The band portion has a distal end, a proximal end and a longitudinal axis therebetween. The band portion is attached to the balloon portion along an inner face thereof. When the device is in its undeployed shape at least a portion of the band portion has a concave cross section taken perpendicular to the longitudinal axis.

13 Claims, 4 Drawing Sheets

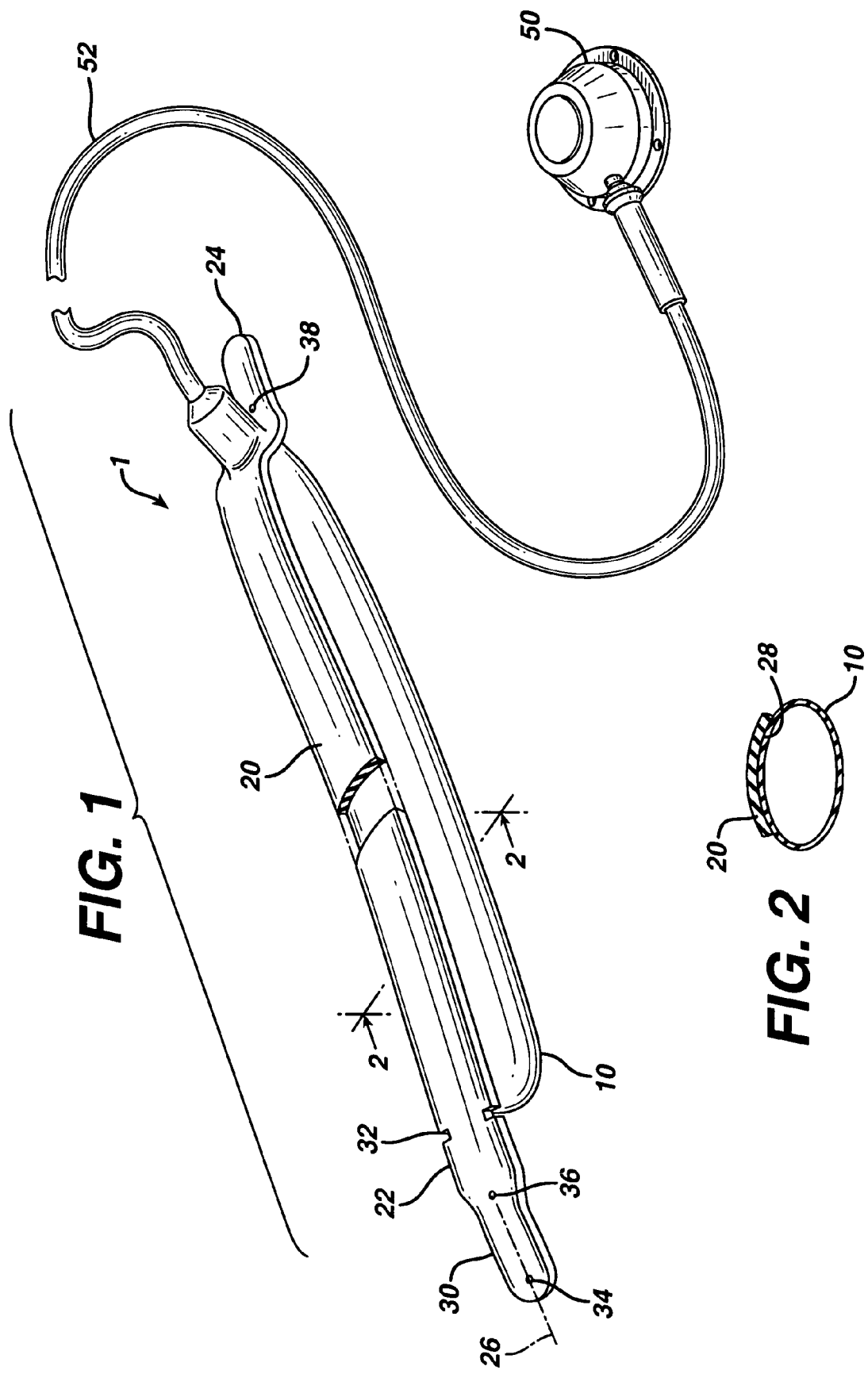

SURGICALLY IMPLANTABLE ADJUSTABLE BAND HAVING A FLAT PROFILE WHEN IMPLANTED

FIELD OF THE INVENTION

The present invention has application in conventional endoscopic and open surgical instrumentation as well as application in robotic-assisted surgery. The present invention has even further relation to adjustable surgically implantable bands, such as gastric bands for the treatment of obesity.

BACKGROUND OF THE INVENTION

The percentage of the world's population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacological methods have all been tried, and failed to correct the condition. Mechanical apparatuses for insertion into the body through non-surgical means, such as the use of gastric balloons to fill the stomach have also been employed in the treatment of the condition. Such devices cannot be employed over a long term, however, as they often cause severe irritation, necessitating their periodic removal and hence interruption of treatment. Thus, the medical community has evolved surgical approaches for treatment of morbid obesity.

Most surgical procedures for treatment of morbid obesity may generally be classified as either being directed toward the prevention of absorption of food (malabsorption), or restriction of stomach to make the patient feel full (gastric restriction) The most common malabsorption and gastric restriction technique is the gastric bypass. In variations of this technique, the stomach is horizontally divided into two isolated pouches, with the upper pouch having a small food capacity. The upper pouch is connected to the small intestine, or jejunum, through a small stoma, which restricts the processing of food by the greatly reduced useable stomach. Since food bypass much of the intestines, the amount of absorption of food is greatly reduced.

There are many disadvantages to the above procedure. Typically the above mentioned procedure is performed in an open surgical environment. Current minimally invasive techniques are difficult for surgeons to master, and have many additional drawbacks. Also, there is a high level of patient uneasiness with the idea of such a drastic procedure which is not easily reversible. In addition, all malabsorption techniques carry ongoing risks and side effects to the patient, including malnutrition and dumping syndrome.

Consequently, many patients and physicians prefer to undergo a gastric restriction procedure for the treatment of morbid obesity. One of the most common procedures involves the implantation of an adjustable gastric band. Examples of an adjustable gastric band can be found in U.S. Pat. No. 4,592,339 issued to Kuzmak; RE 36176 issued to Kuzmak; U.S. Pat. No. 5,226,429 issued to Kuzmak; U.S. Pat. No. 6,102,922 issued to Jacobson and U.S. Pat. No. 5,601,604 issued to Vincent, all of which are hereby incorporated herein by reference. In accordance with current practice, a gastric band is operatively placed to encircle the stomach. This divides the stomach into two parts with a stoma in-between. An upper portion, or a pouch, which is relatively small, and a lower portion which is relatively large. The small partitioned portion of the stomach effectively becomes the patients new stomach, requiring very little food to make the patient feel full.

Once positioned around the stomach, the ends of the gastric band are fastened to one another and the band is held securely in place by folding a portion of the gastric wall over the band and closing the folded tissue with sutures placed therethrough thereby preventing the band from slipping and the encircled stoma from expanding. Prior art gastric bands can best be described by referring to FIGS. 5 and 6. Prior art gastric band 101 includes a flexible substantially non-extensible portion 120 having an expandable, inflatable portion 110 attached thereto. Inflatable portion 110 is in fluid communication with a remote injection site. Injection or removal of an inflation fluid into or from the interior of the expandable shell is used to adjust the size of the stoma either during or following implantation. By enlarging the stoma, the patient can eat more food without feeling as full, but will not lose weight as fast. By reducing the size of the stoma, the opposite happens. Physicians regularly adjust the size of stoma to adjust the rate of weight loss.

For most bands, as seen from FIG. 5, the flexible substantially non-extensible portion 120 of the band 101 has a flat rectangular profile prior to placement within the body. However, as seen from FIG. 6, when it is implanted around the stomach 111 the portion 120 strains and deforms, which causes its surface to bend and take on a convex profile. This creates potential sharp points 121 on the band. This is also a cosmetic and perceived quality issue. Therefore, there has been a need for an adjustable gastric band which does not bend as such when implanted.

SUMMARY OF THE INVENTION

In accordance with the present invention, there is provided an implantable surgical device having a deployed shape and an undeployed shape. The device includes an elongated flexible inflatable balloon portion and an elongated flexible and substantially inextensible band portion. The band portion has a distal end, a proximal end and a longitudinal axis therebetween. The band portion is attached to the balloon portion along an inner face thereof. When the device is in its undeployed shape at least a portion of the band portion has a concave cross section taken perpendicular to the longitudinal axis.

DETAILED DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 1 is a perspective view of a device 1, made in accordance with the present invention.

FIG. 2 is a cross section of the device shown in FIG. 1, taken along lines 2-2.

DETAILED DESCRIPTION OF THE INVENTION

Figure 5:
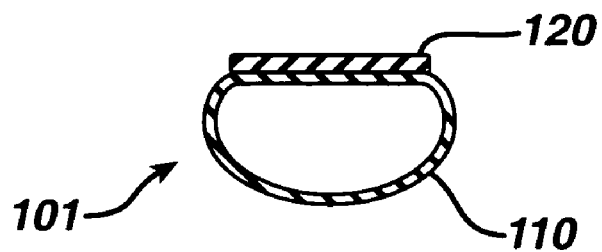
FIG. 5 is a view similar to that of FIG. 2, but showing a prior art device 101.

Referring now to the drawings wherein like numerals indicate the same elements throughout the views, as stated above there is shown in FIG. 5 a prior art adjustable gastric band of the type described in the above mentioned incorporated references. The device 101 includes an elongated flexible inflatable portion, alternatively referred to as balloon portion, 110 and an elongated flexible and substantially inextensible band portion 120. FIG. 5 shows the device in its undeployed shape, with band portion 120 with a flat profile having a linear cross-section.

Figure 6:
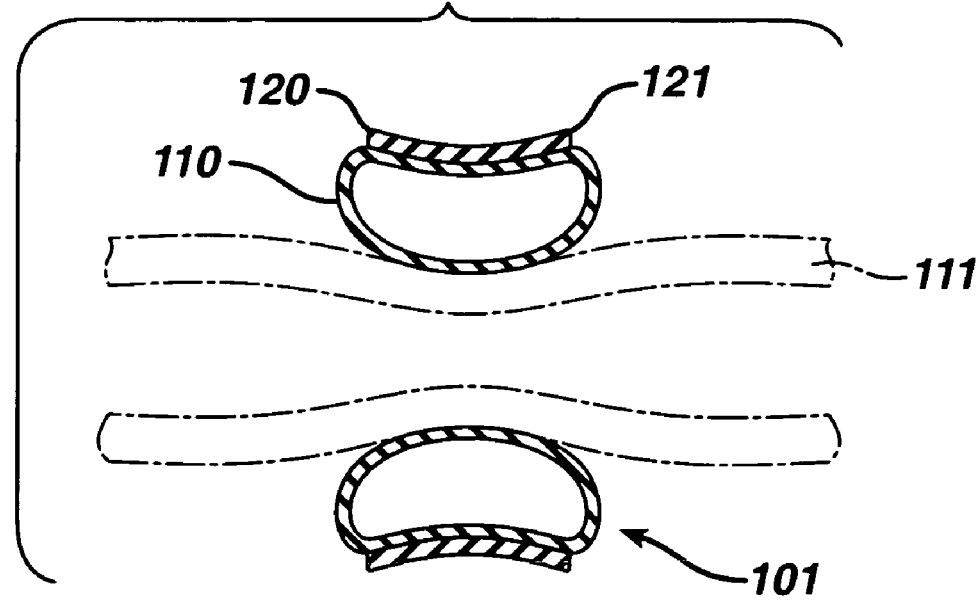
FIG. 6 is a cross sectional view of band 101, but showing it in its deployed position.

As stated above, however, and as seen from FIG. 6, once the device 101 is positioned around the stomach 111, and the ends of the gastric band are fastened to one another, band portion 120 strains and deforms, which causes its surface to bend and take on a convex profile. This creates potential sharp points 121 on the band, which are also a cosmetic and perceived quality issue. Therefore, there has been a need for an adjustable gastric band which does not bend when implanted and take on a concave profile.

Referring now to FIG. 1, there is shown a surgically implantable device 1 made in accordance with the present invention. The device includes an elongated flexible inflatable balloon portion 10. Balloon portion can be made from any number of materials known to those skilled in the art including silicone and polyurethane]. Device 1 further includes and an elongated flexible and substantially inextensible band portion 20. The band portion has a distal end 22, a proximal end 24 and a longitudinal axis 26 therebetween. Band portion 20 can be made from any number of materials known to those skilled in the art including silicone and polyurethane. The band portion is attached to the balloon portion along an inner face 28 (shown in FIG. 2) of the band portion 20. The inflatable or balloon portion 10 can be attached to band portion 20 by any number of means known to those skilled in the art including using a silicone adhesive. The two portions may also be integrally manufactured as one part.

The distal and proximal ends of the band portions preferably include means for attaching such ends together. There are various means for attaching the distal and proximal ends of the band together. Many of these are described in co-pending and commonly assigned U.S. patent application Ser. No. 60/483,353 filed Sep. 30, 2003, 60/507,916 filed Sep. 30, 2003 and 60/507,625 filed Sep. 30, 2003 the disclosures of which are hereby incorporated herein by reference. FIG. 1 shows the distal end of the band 22 as comprising a tab 30 having notches 32. This tab 30 would be inserted into a slot (not shown) on the proximal end 24 of band 20. Tab 30 also includes suture holes 34 and 36, one of which would line up with suture hole 38 on the proximal end 24 of band 20. After the tab 30 is inserted into the slot, and the physician is pleased with the final position of the band, the ends 22 and 24 are then often sutured together to better secure the band in position. However, many alternative locking means, such as those described in the above incorporated reference, do not need to use suture.

Inflatable portion 10 is shown as being in fluid communication with an injection port 50 via a fluid line 52. However, inflatable portion 10 could also be fluidly connected to an implanted reservoir such as those used with remotely controlled bands. Such a band is described in U.S. Pat. No. 6,453,907 issued on Sep. 24, 2002, which is hereby incorporated herein by reference. Port 50 is of the type well known in the medical field not only for gastric bands, but such ports are also used for vascular access for drug delivery. After device 1 is implanted into a patient, port 50 is attached just below the skin of the patient, so that fluid can be inserted and withdrawn from the inflatable portion with a syringe. Fluid line 52 can be integral with inflatable portion 10 or can be a separate piece.

Figure 3:
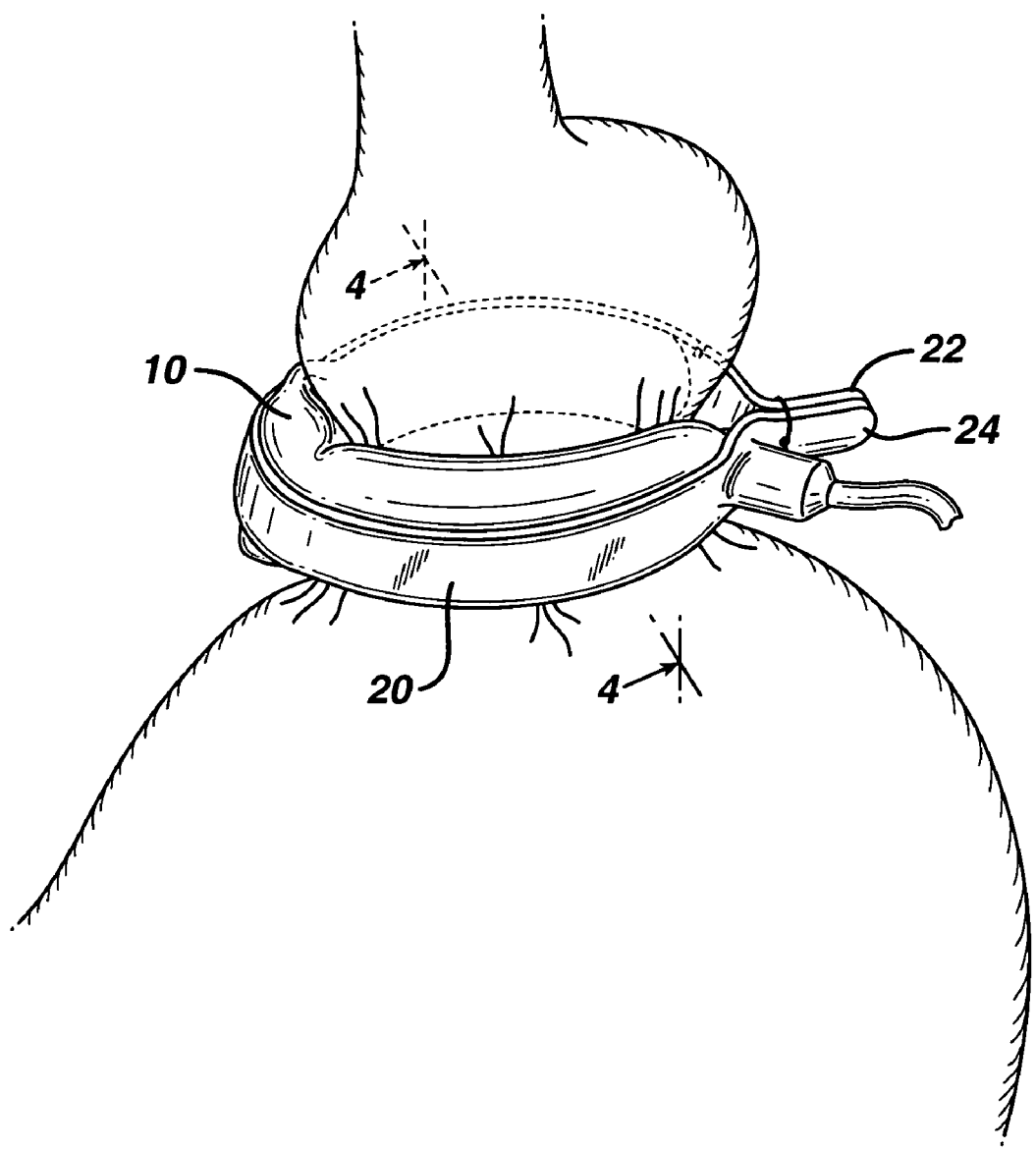
FIG. 3 is a perspective view of a device 1 showing it in its deployed position.

Device 1 has an undeployed position with an undeployed shape shown in FIG. 1. This is the shape and position of the device prior to the device being inserted into a patient. Device 1 also has a deployed position with an deployed shape, shown in FIG. 3. The deployed position of the band is when the band is encircling a body part of the patient, such as the stomach or esophagus. FIG. 3 shoes the band having ends 22 and 24 attached to each other both with the tab and slot and the suture.

Figure 4:
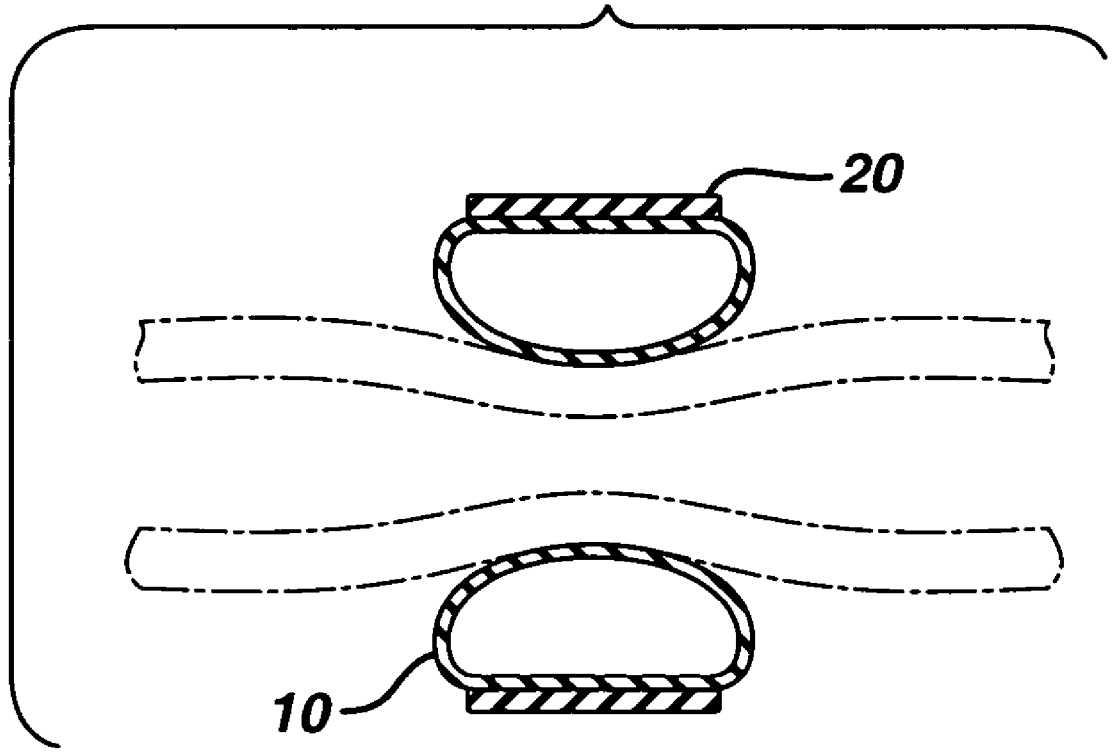
FIG. 4 is a cross section of the device shown in FIG. 3, taken along lines 4-4.

FIG. 2 shows a cross section of inflatable portion 10 and band portion 20 when the device 1 is in its undeployed position. As seen from the figure, when the device is in its undeployed shape band portion 20 has a concave cross section taken perpendicular to longitudinal axis 26. The band portion 20 is molded in the present shape. The advantage of this can be seen by referring to FIG. 4. FIG. 4 shows a cross section of inflatable portion 10 and band portion 20 when the device 1 is in its deployed position. As the seen from that figure, the concave nature of the band 20 in its undeployed state, causes it to take on a substantially linear cross-section, or flat profile, when the device is in its deployed state. Compare this to FIG. 6, wherein when the band has a flat profile in its undeployed state, it takes on a concave profile or shape in its deployed state. Therefore, the above described device has a band portion 20 which strains and deforms when implanted, but causes its surface to bend and take on a flat profile. This eliminates any potential sharp points or a cosmetic and perceived quality issues.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. patent application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. patent application 2003/0114729 which is hereby incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, as would be apparent to those skilled in the art, the disclosures herein have equal application in robotic-assisted surgery. In addition, it should be understood that every structure described above has a function and such structure can be referred to as a means for performing that function. Accordingly, it is intended that the invention be limited only by the spirit and scope of the appended claims.

What is claimed is:

1. An implantable surgical device having a deployed shape and an undeployed shape, said device comprising:
   a. an elongated flexible inflatable portion; and
   b. an elongated flexible and substantially inextensible band portion having a distal end, a proximal end and a longitudinal axis therebetween, said band portion being attached to said inflatable portion along an inner face thereof, wherein when said device is in its undeployed shape said band portion has a concave cross section along a majority of its longitudinal axis, taken perpendicular to said longitudinal axis, and wherein when said device is in its deployed shape said band portion has a substantially linear cross section along a majority of its longitudinal axis.

2. The device of claim 1 wherein said inflatable portion and said band portion are integrally manufactured as one part.

3. The device of claim 1 wherein said band portion in its deployed shape has a substantially flat cross section, taken perpendicular to said longitudinal axis.

4. The device of claim 1 wherein said band portion is at least partially made from at least one of silicone and polyurethane.

5. The device of claim 1 further comprising a means for attaching said distal and proximal ends of said band together.

6. The device of claim 1 further comprising an injection port in fluid communication with said inflatable portion.

7. An implantable surgical device having a deployed shape and an undeployed shape, said device comprising:
   a. an elongated flexible band portion having a distal end, a proximal end and a longitudinal axis therebetween, wherein when said device is in its undeployed shape said band portion has a concave cross section along a majority of its longitudinal axis, taken perpendicular to said longitudinal axis, and wherein when said device is in its deployed shape said band portion has a substantially liner cross section along a majority of its longitudinal axis; and
   b. a means for attaching said distal and proximal ends of said band together.

8. The device of claim 7 wherein said band portion in its deployed shape has a substantially flat cross section, taken perpendicular to said longitudinal axis.

9. The device of claim 7 wherein said band portion is at least partially made from at least one of silicone and polyurethane.

10. An implantable surgical device having a deployed shape and an undeployed shape, said device comprising:
    a. an elongated flexible inflatable portion;
    b. an elongated flexible and substantially inextensible band portion having a distal end, a proximal end and a longitudinal axis therebetween, said band portion being attached to said inflatable portion along an inner face thereof, wherein when said device is in its undeployed shape said band portion has a concave cross section along a majority of its longitudinal axis, taken perpendicular to said longitudinal axis, and wherein when said device is in its deployed shape said band portion has a substantially linear cross section along a majority of its longitudinal axis;
    c. a means for attaching said distal and proximal ends of the band together; and
    d. an injection port in fluid communication with said inflatable portion.

11. The device of claim 10 wherein said inflatable portion and said band portion are integrally manufactured as one part.

12. The device of claim 10 wherein said band portion in its deployed shape has a substantially flat cross section, taken perpendicular to said longitudinal axis.

13. The device of claim 10 wherein said band portion is at least partially made from at least one of silicone and polyurethane.

* * * * *